United States Patent [19]

Fujimaki

[11] Patent Number: 4,510,161

[45] Date of Patent: Apr. 9, 1985

[54] ANTIHYPERTENSIVE AGENTS AND PROCESS FOR PRODUCING THE SAME

[75] Inventor: Akira Fujimaki, Koganei, Japan

[73] Assignee: Zaidan Hojin Minsei Kagaku Kyokai, Koganei, Japan

[21] Appl. No.: 435,350

[22] Filed: Oct. 20, 1982

[30] Foreign Application Priority Data

Oct. 22, 1981 [JP] Japan .................................. 56-169157

[51] Int. Cl.³ .............................................. A61K 35/78
[52] U.S. Cl. ..................................................... 514/54
[58] Field of Search ....................... 424/180, 199, 364; 260/428.5

[56] References Cited

U.S. PATENT DOCUMENTS 4,154,750  5/1979  Moore et al. ..................... 260/428.5

OTHER PUBLICATIONS

*Chemical Abstracts,* 94:155460q (1981) [Mogenson, G., et al., *Nutr. Rep. Int.* 1981, 23(3), 411–418].

*Chemical Abstracts,* 95:181649y (1981) [Tokumura, A., et al., *J. Pharmacol. Exp. Ther.,* 1981, 219(1), 219–224].

*Primary Examiner*—Richard A. Schwartz
*Attorney, Agent, or Firm*—Oblon, Fisher, Spivak, McClelland & Maier

[57] ABSTRACT

An aqueous extract product which is effective for prevention or treatment of hypertension is produced by: concentrating an aqueous extract obtained by: extracting water-soluble components from vegetable oils such as soybean oil, corn oil, rapeseed oil and cotton seed oil; adding a lower alcohol to the resulting extract to prepare an alcoholic solution having an alcohol concentration above 85%, thereby precipitating the insoluble matter; then removing the precipitates; and thereafter removing the alcohol. A powdered product having an antihypertensive activity is also produced by: subjecting said aqueous extract product to an additional optional purification step and thereafter concentrating the resulting product to obtain a powder. An antihypertensive agent containing a novel substance OSG as an effective component is also disclosed.

18 Claims, 2 Drawing Figures

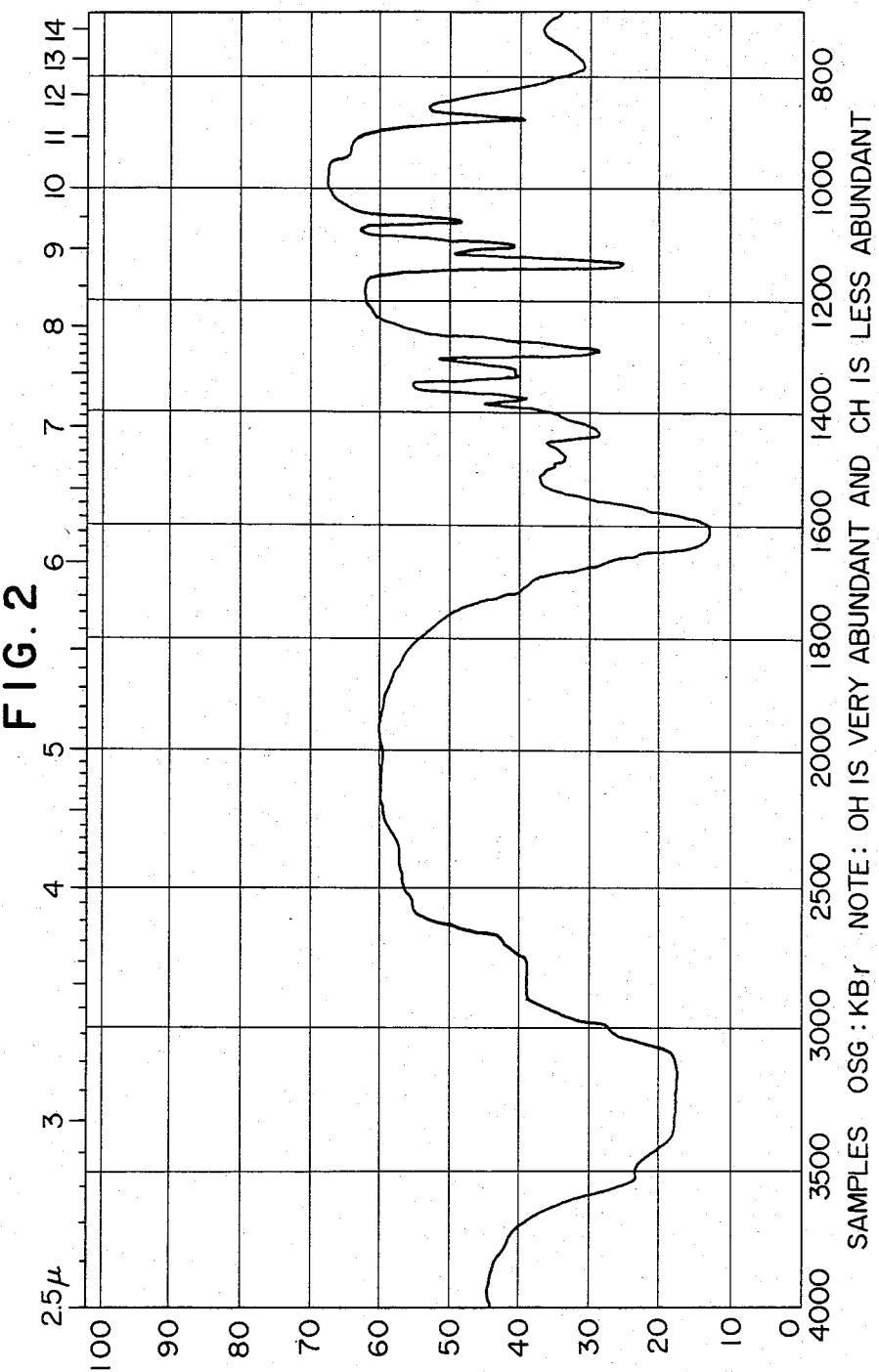

ANTIHYPERTENSIVE AGENTS AND PROCESS FOR PRODUCING THE SAME

BACKGROUND OF THE INVENTION

1. Field of the Invention

The present invention relates to a process for extraction and purification of an antihypertensive agent containing a substance useful for prevention or treatment of hypertension from vegetable oils such as soybean oil, corn oil, rapeseed oil and cotton seed oil, and to a novel substance useful for prevention or treatment of said hypertension.

2. Background Art

Vegetable oils such as soybean oil and the like are generally produced by pulverizing seeds such as soybean seed and then compressing the pulverized seeds at lower temperatures or elevated temperatures. Particularly, soybean oil is produced on a large scale by an extraction method wherein organic solvents such as hexane and the like are used.

However, there has been almost no attempt to effectively utilize the water-soluble components present in the vegetable oils such as soybean oil and the like, and most of the water-soluble components are at present being discarded as waste. Furthermore, to date, almost no investigation has been undertaken to determine structures and properties of the water-soluble components present in these vegetable oils. Some reasons why the water-soluble components present in these vegetable oils are not effectively utilized, are as follows: these water-soluble components present in the vegetable oils comprise extremely various compounds and therefore it is difficult to separate and purify each component, and, moreover, it is difficult to distinguish between useful components and useless components.

SUMMARY OF THE INVENTION

I have carried out studies with the object of effectively utilizing the water-soluble components present in the vegetable oils such as soybeam oil and the like which components have hitherto been discarded as a valueless waste. I have found that when an alcohol is added to a solution containing water-soluble components which have been extracted from such vegetable oils so as to prepare an alcoholic solution having an alcohol concentration of 85% or higher, gummy matter, protein and the like present in the extract are satisfactorily and completely separated, and a substance having antihypertensive activity is present in a mother liquor. I have developed the present invention on the basis of above discovery, which has not been anticipated in the prior art as far as I am aware. Further, the above mentioned substance having antihypertensive activity not only has antihypertensive activity but also can reduce blood pressure gradually or slowly. Furthermore, when this substance is administered to normal humans, little side reaction is observed. In addition, this substance is expected to have an effect of strengthening blood vessels.

BRIEF DESCRIPTION OF THE DRAWINGS

In the drawings:

FIG. 2 is an infrared spectrum chart of the objective substance of the present invention.

DETAILED DESCRIPTION

Figure 1:
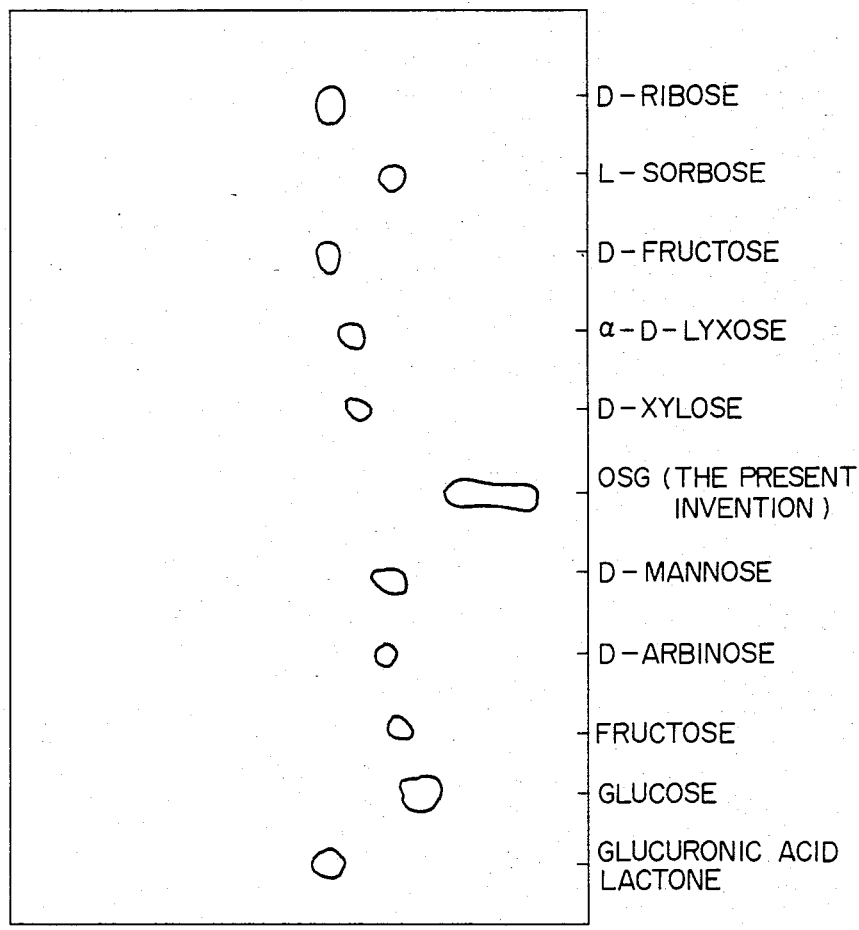
FIG. 1 is a paper chromatograph in which an objective substance of the present invention is compared with a variety of known compounds.

Vegetable oils which are starting materials in the present invention include soybean oil, corn oil, rapeseed oil, and cotton seed oil. Particularly preferred are soybean oil and corn oil. Because oil cakes or foots wherein a portion of vegetable oil is already squeezed out from seeds such as soybean and corn seeds may contain a large amount of the vegetable oil, such oil cakes or foots may be used as the vegetable oils which are starting materials in the present invention.

While these vegetable oils may contain vegetable dyestuff such as chlorophyll, carotenoid, sterols or vitamins such as tocopherol, these components do not migrate into the aqueous solvent in the extraction of the oil with an aqueous solvent because these components have low solubility in water. Accordingly, it is not necessary to remove these water-insoluble components in subsequent purification steps.

The substance useful for prevention or treatment of hypertension is separated and purified from these vegetable oils as described hereinafter.

These vegetable oils are first brought in contact with an aqueous solvent to extract water-soluble components present in the vegetable oils with the aqueous solvent. Suitable aqueous solvents for use in this invention are water, warm water or a mixture of water and an alcohol. Suitable alcohols for use in this invention are lower alcohols such as methanol, ethanol and the like. While the proportion of water to alcohol may widely vary, it is desirable to use a mixture of from 10% to 90% by volume of water and from 90% to 10% by volume of alcohol, and preferably a mixture of from 10% to 40% by volume of water and from 90% to 60% by volume of alcohol. Preferably, for contact with the vegetable oil, the aqueous solvent is used in an amount of from 1 to 5% by weight of the vegetable oil. Additionally, the use of the mixture of water and alcohol has the effect of preventing fermentation and putrefaction of the aqueous extract.

The aqueous extract thus obtained is concentrated. When an alcohol is added to the resulting concentrated solution to form an alcoholic solution having an alcohol concentration of 85% or more, impurities such as gummy matter, protein and the like are precipitated as insoluble matter. When the precipitate is removed and then alcohol is removed by vacuum distillation or the like, an aqueous extract product containing the desired components in concentrated form can be obtained.

The settling and separation of gummy matter and protein can be carried out in above treatment even if the alcohol concentration is less than 85%. However, the separation is insufficient and a portion of gummy matter and protein may remain in the mother liquor. When gummy matter and protein remain in the mother liquor, many difficulties are encountered in the subsequent purification steps. Thus, such residue is not desirable. Accordingly, any alcohol concentration above 85% can be used in this treatment. However, it is preferable to use a concentration below 90% from the standpoint of industrial economy.

Because the aqueous extract product thus prepared already contains the required effective components in a considerably concentrated form, a sufficient function of reducing blood pressure can be attained even if it is applied to a living animal as it is. A further purified effective substance can be obtained by adding water to the aqueous extract product, treating the resulting solution with active carbon, then separating and removing from the mother liquor the compounds which deposit and precipitates at a sugar content on a Brix scale of about 50%, and thereafter drying the purified mother liquor into a white powder.

It has been found that compounds which deposit and precipitates at a sugar content on the Brix scale of about 50% include magnesium lactate according to my analysis.

It has been found that magnesium lactate will deposit optimally at a sugar content on the Brix scale of about 50%.

Since the presence of magnesium lactate has been found, the aqueous extract product can be purified by subjecting it to a carbon column chromatography to fractionate and purify the effective component.

While the presence of magnesium lactate in soybean oil was not heretofore known, I have found that magnesium lactate is present in soybean oil by the following procedure. The compounds are separated as described above, then recrystallized several times, and thereafter measured by elemental analysis, angle of rotation, infrared absorption spectrum (IR), ultraviolet absorption spectrum (UV), gas chromatograph (GC), and nuclear magnetic resonance (NMR). The metal element is identified and determined. As a result, the crystal obtained is determined to be magnesium lactate $MgC_6H_{10}O_6$.

When magnesium lactate was administered to spontaneously hypertensive rats (SHR) and adult dogs to carry out an animal experiment, no antihypertensive activity was observed. On the other hand, it has been found that when the mother liquor from which magnesium lactate has been separated or the substance containing sugar components isolated therefrom is administered to the spontaneously hypertensive rats (SHR) and humans, the antihypertensive activity can be obtained. Thus, it has been found that the materials as described above are effective for hypertension. This is described in detail hereinafter.

When the mother liquor from which magnesium lactate-based precipitates have been completely removed or separated is concentrated, a crystalline powder is obtained. It is possible to recrystallize this crystalline powder to purify it. This cyrstalline powder or the crystals obtained by recrystallization is a novel substance the presence of which has not been known to date. This novel substance has the following features. The novel substances of the present invention exhibits a color reaction of sugar in the α-naphthol reaction and orcinol reaction, is negative in TCA reaction and ninhydrin reaction, and is positive in glycyrrhizin reaction. When this substance is subjected to a paper chromatograph method, no spots consistent with those of known sugars are observed. A hydrolyzate of the substance exhibits a spot consistent with that of glucose or sorbose and exhibits a sugar lower than that of glucuronic acid. Further, the present substance is confirmed to be a polymeric sugar by infrared absorption spectrum and $^1HNMR$ spectrum methods. The present substance having these features is hereinafter referred to as OSG.

Chemical properties of the novel substance OSG are described hereinafter together with a portion of the results of tests performed thereon.

(a) The OSG exhibits the color reaction of sugar in α-naphthol reaction (Molisch reaction) of orcinolhydrochloric acid reaction (Bial reaction).

(b) The OSG is negative in TCA (trichloroacetic acid) reaction and ninhydrin reaction, and positive in glycyrrhizin reaction.

(c) When the OSG is developed using a PPC method (Whatman No. 1, a developing solvent nBuOH:AcOH:H$_2$O 4:1:5) and then is colored with aniline phthalate, a retention time of the OSG is not consistent with that of any compound such as D-ribose, L-sorbose, D-fructose, α-D-lyxose, D-xylose, D-mannose, D-arabinose, fructose, glucose, or glucuronic acid lactone. Reference is made to the paper chromatograph of FIG. 1.

(d) A hydrolyzate obtained by hydrolyzed the OSG according to the present invention with 10% $H_2SO_4$ was identified by a PPC method (Whatman No. 1; a color reagent:naphthol, resorcinol-trichloroacetic acid; solvent; α-collidine-saturated water).

As a result, the sugar obtained by hydrolyzing the OSG exhibited spots which are consistent with those of glucose and sorbose and a spot the Rf value of which is lower than that of glucuronic acid.

(e) An attempt to identify the OSG by gas chromatography was made.

The OSG was converted to form a trimethyl silyl derivative, and then analysis and identification were carried out by means of a gas chromatograph method. Analytical conditions: OV-17 (methyl phenyl (50%)-silicon filler); 3% gas column Q stainless-steel, 2 meters; and a temperature of the column of 180° C.

The retention time obtained is very close to that of fructose, but slightly shifted. No peaks which are consistent with those of other known sugars are observed.

(f) An attempt to identify the sugar by gas chromatograph was made.

A sugaralcohol obtained by reduction with NaBH$_4$ was first acetylated to prepare a sample, and this sample was analyzed under the following conditions: 3% OV-17 gas column Q stainless-steel column, 2 meters, a temperature of the column of 230° C., and FID detection. The retention time obtained was consistent with that of sugaralcohol acetates derived from fructose, glucose and mannose. These were some other peaks which could not be identified.

(g) The results determined by the $^1HNMR$ spectrum method (60 MHz, d-DMSO) showed that the OSG comprises a number of molecules bonded to each other. However, the molecular structure could not be specified therefrom.

(h) An infrared spectrum chart of the OSG is shown in FIG. 2. In the spectrum of FIG. 2, there were hydroxyl groups of polymeric compound at 3100–3550 cm$^{-1}$, alkyl groups at 2700–3000 cm$^{-1}$, carboxylate groups at 1600 cm$^{-1}$, alcohol at 1420 cm$^{-1}$ and a variety of groups at a frequency lower than 1420 cm$^{-1}$. Substances having such an infrared spectrum have been unknown.

EXAMPLE 1

A raw oil (80 tons) obtained by treating soybeans with hexane to extract soybean oil and then removing oil cakes or foots by a separator for oil cakes or foots is brought into contact with water or warm water in an amount of about 5% by weight of said raw oil to obtain 4,000 liters of an aqueous extract. If oil and water are admixed with vigorous shaking or stirring, emulsification will take place, and it will be difficult to carry out subsequent separation procedures. Accordingly, care must be taken to avoid vigorous shaking of the mixture. For example, it is desirable to use a drop extraction method wherein an extracting solvent is added dropwise.

Water acidified with organic acids or mineral acids (a pH of from 3.0 to 4.9) or neutral water (a pH of from 5.0 to 7.0) or warm neutral water can be also used as the extracting solvent. When acidic extracting solvents are used, an alkali is preferably added to make the solution neutral after extraction.

About 4,000 liters of the aqueous solution (a pH of 6.8) obtained by contact extraction is vacuum distilled at a temperature below 40° C. to concentrate it to about 1/40 of its original volume, thereby obtaining 100 kg of a black brown concentrated solution having a sugar content on the Brix scale of about 47%. Methyl alcohol (99%) is added to the concentrated solution in the same volume or a volume twice the volume of the solution with stirring to deposit and precipitate insoluble matter. Such insoluble matter is filtered off and removed. The filtrate thus obtained is vacuum distilled to remove alcohol. Thus, a concentrated aqueous extract is obtained. The above mentioned addition of methyl alcohol tends to prevent fermentation of the extract.

Methyl alcohol is further added to the aqueous extract to prepare an alcoholic solution having an alcohol concentration of 85%, whereby a large amount of gummy matter, protein and the like are deposited and precipitated. The resulting solution is allowed to stand overnight, and the precipitates are filtered off. Then, the filtrate thus obtained is vacuum distilled to recover alcohol, whereby about 50 kg of considerably purified aqueous extract product can be obtained. The sugar content on the Brix scale of this aqueous extract product is about 50%. This aqueous extract product is a main starting material for OSG as described hereinafter.

Purified water is added to 500 g of the aqueous extract product thus obtained to dilute the same. Thus, a diluted solution having a sugar content on the Brix scale of 30% is obtained. An appropriate amount of activated carbon is added to the diluted solution. Thus, impurities are adsorbed by the activated carbon to obtain a colorless or slightly yellow, clear aqueous extract.

The sugar content adsorbed onto activated carbon is eluted with hot water until no sugar content effuses. Then, this eluant and the aqueous extract (below 35%) are combined and then concentrated under reduced pressure to prepare a solution having a sugar content on the Brix scale of 50%, from which are deposited needle-like crystals. To examine the relation between the quantity of these crystals deposited and the sugar content of the mother liquor, various solutions respectively having sugar contents on the Brix scale of 20%, 30%, 40% and 50% are prepared. When the sugar content on the Brix scale is 50%, the quantity of crystals deposited is maximal.

Then, the crystal thus obtained is washed with 99% alcohol and repeatedly recrystallized to deposit glossy white needle-like magnesium lactate crystals. Activated carbon is added to the mother liquor, from which magnesium lactate-based precipitates depositing at a sugar content on the Brix scale of about 50% have been separated and removed. Thus, the mother liquor is treated with activated carbon to obtain a colorless clear aqueous solution. This aqueous solution is concentrated and lyophilized to obtain 112 grams of a white hygroscopic powder. This is the objective OSG of the present invention.

EXAMPLE II

The oil cakes or foots obtained in an initial stage of the extraction step of soybean oil contain OSG of the present invention in addition to sterols, vegetable dyestuffs and tocopherols. Thus, an alcohol-water mixture of from 50% to 75% of alcohol and from 50% to 25% of water is added to soybean oil foots separated by means of a separator for oil foots. The reaction mixture is stirred or shaken, or extracted under heating by using a reflux condenser to dissolve effective components present in the soybean oil foots in the alcohol-water mixture medium.

This alcohol-water mixture medium is vacuum distilled at a temperature below 35° C. to remove alcohol, and 99% methyl alcohol is added to the resulting aqueous extract to prepare an alcoholic solution having an alcohol concentration of 85%. Thus, insoluble matter such as gummy matter, protein and the like are deposited and precipitated. The insoluble matter is removed from the extract, and then the alcoholic solution is vacuum distilled to recover alcohol.

Purified water is added to the aqueous extract product thus obtained, and thereafter activated carbon is added thereto in the same manner as in Example I. The resulting colorless clear aqueous solution is vacuum distilled at a temperature of below 35° C. to prepare a solution having a sugar content on the Brix scale of 50%. Thus, magnesium lactate precipitates. The magnesium lactate is removed, and 99% methyl alcohol is added to the resulting aqueous extract to prepare a clear alcoholic solution having an alcohol concentration about 85%.

Acetone is added to 1 liter of the clear alcoholic solution with stirring to form a large quantity of cloudy deposits. When acetone is added to the methanol solution in a volume of about twice the volume of the solution, deposition and precipitation are greatly facilitated and therefore use of such a quantity is preferred.

The reaction mixture is allowed to stand overnight to separate the mother liquor from the deposited precipitates. In this case, a large portion of the inorganic material passes into the separated mother liquor. The deposited precipitates are subjected to vacuum drying to obtain 74 grams of OSG in the form of a slightly yellow hygroscopic powder.

EXAMPLE III

An 85% methanol solution (500 ml) obtained by removing gummy matter, protein and the like in the same manner as in Example I is vacuum distilled to remove the methanol. Thus, a solution having a sugar content on the Brix scale of 80% (a refractive index of 1.495) is obtained. To this solution is added 200 ml. of purified water to prepare 265 ml. of a brown clear solution having a sugar content of the Brix scale of 29.5%. The resulting solution is then subjected to an activated carbon column chromatograph.

More specifically, 200 grams of activated carbon is slurried with water, and air is removed by a vacuum treatment. The treated activated carbon is then poured into a glass tube of 4.8-cm diameter. The final height of the treated activated carbon is about 28 cm. A circular filter paper is mounted onto the upper portion of the column, and 265 ml. of the brown clear aqueous solution is gently poured at a flow rate of about 5 ml. per 30 minutes onto the circular filter paper to cause adsorption development thereof.

The adsorbed carbon removed from the glass tube in an extrusion manner is cut every 2 cm from the top to obtain fractions Nos. 1 through 12. To each fraction of the carbon is added 100 ml. of 50% methanol, and an extraction procedure is carried out for 5 minutes using a reflux condenser. The extracts are examined by an α-naphthol reaction method to check the color reaction of sugar. The fractions Nos. 1 through 7 are positive in an α-naphthol reaction, and the reaction boundary is colored reddish purple (sugar). The fraction No. 8 exhibits both bluish yellow (magnesium lactate) and raddish purple (sugar). The fractions Nos. 9, 10, 11, and 12 exhibit only slightly yellow. Of course, the eluates of these fractions Nos. 9 through 12 exhibit no color reaction of sugar.

The eluates of the fractions Nos. 1 through 7 are combined, concentrated under reduced pressure at a temperature of 35° C., and lyophilized to obtain a white hygroscopic powder OSG.

EXAMPLE IV

Purified water (700 ml.) is added to a white or pale yellow powder obtained by purifying the aqueous extract product as described in Example I to obtain 1,000 ml. of an aqueous solution having a sugar content on the Brix scale of 20%. The aqueous solution is then passed through a column packed with a mixture of an anionic exchange resin Amberlite IRA-410 and a cationic exchange resin Amberlite IR-120B to further adsorb impurities to carry out further purification.

In addition to water for the reaction, additional wash water is passed through the column, and the exchange resins are washed with the additional water until α-naphthol reaction becomes negative. The eluate and the washings are vacuum distilled to obtain colorless clear concentrated aqueous solutions, respectively. Both solutions are combined and lyophilized to obtain 112 grams of a powder having no hygroscopicity. This powder is recrystallized from a mixture of water and ethanol to obtain a colorless needle-like substance having a melting point of from 146° to 155° C.

EXAMPLE V

Corn oil is brought into contact with water or warm water in an amount of about 5% by weight of said oil to obtain an aqueous extract. The aqueous extract is vacuum distilled to obtain a concentrated solution having a sugar content on the Brix scale of about 50%. Methyl alcohol (99%) is added to the concentrated solution in a volume twice the volume of the solution to deposit and precipitate gummy matter. The above-mentioned of methyl alcohol tends to prevent fermentation of the solution. Such gummy matter is filtered off and removed. The filtrate thus obtained is vacuum distilled to remove alcohol to prepare a concentrated filtrate having an alcohol concentration of about 75%. Methyl alcohol is added to the concentrated filtrate to prepare an alcoholic solution having an alcohol concentration of 85%, whereby a small amount of insoluble matter is deposited and precipitated. The insoluble matter is filtered off to obtain a clear solution. The solution is concentrated under reduced pressure to obtain a pale yellow hygroscopic powder OSG.

EXAMPLE VI

Wheat germ oil is brought into contact with water or warm water in an amount of about 5% by weight of said oil to obtain an aqueous extract. The aqueous extract is vacuum distilled to prepare a concentrated aqueous solution.

Methyl alcohol (99%) is added to the concentrated aqueous solution to prepare an alcoholic solution having an alcohol concentration of 85%, whereby a small amount of insoluble matter is deposited and precipitated. The insoluble matter is filtered off to obtain a clear solution. The solution is concentrated under reduced pressure to obtain a pale yellow hygroscopic powder OSG.

The following experimental results illustrate the effects and influences caused by the administration of OSG according to the present invention to living animals.

(A) Test for examining an antihypertensive activity caused by administering OSG to spontaneously hypertensive rats (SHR) and normal rats.

I. Animals

Control group: Normal Wistar rat, male, 5 rats per group.

Test group (1): Normal Wistar rat, male, 5 rats per group.

Test group (2): SHR, male, 6 rats per group.

II. Administration

Samples were orally administered into the stomach by means of a sonde once a day (10 a.m.). Samples were administered continuously for 7 days.

III. Dosage

Control group: Only water was administered to normal rats.

Test group (1): OSG (50 mg/kg) is administered to normal rats in a quantity of 1 ml. per 100 grams of body weight.

Test group (2): OSG (50 mg/kg) is administered to SHR in a quantity of 1 ml. per 100 grams of body weight.

IV. Observation Item

Blood pressure (maximum blood pressure).

V. Sphygmomanometry

An arterial maximum blood pressure at the tail of each rat was determined by using PROGRAMMED ELECTROSPHYGMOMANOMETER PE-300, NARCOBIO SYSTEMS INC.

Results:

I. In the case of each normal rat of Control group and Test group (1), no change was observed.

II. In the case of Test group (2) SHR, use of 50 ml/kg produced antihypertensive activity (average 20 mmHg). The antihypertensive activity was also observed in 3 to 6 hours after administration. While the blood pressure of some rats was restored to substantially original blood pressure after 24 hours, in some cases the value of the blood pressure after 96 hours was still low at a reduction of 18 mmHg. This shows that the continuous administration of OSG affords an antihypertensive activity. Further, the activity was extremely mild. No groups showed toxic symptoms.

(B1) Test for acute toxicity caused by oral administration of OSG.

Agents to be tested: OSG.

Test conditions: Room temperature (23° to 25° C.); humidity of from 55% to 60%.

Animals to be tested: Mice, SLC-ddy male and female (Nippon Ika Dobutsu-sha).
Total number of animals used:
Preliminary test: 15 males; 15 females.
Final test: Five groups, 8 mice per group; 25 males and 22 females.
Average of body weight: Males 23 grams; females 22 grams.
Administration: Oral administration (A sonde for mouse was used).
Calculation: Litchfield and Wilcoxon method.
Test results: For males, $LD_5=13.5$ g/kg (The upper limit was 14.85 g/kg and the lower limit was 12.27 g/kg); for females, $LD_{50}=12.5$ g/kg (The upper limit was 14.6 g/kg and the lower limit was 10.7 g/kg).
General Symptoms:

| After Administration | Defecation | Urination |
|---|---|---|
| Posture | Not specified, many mice were in supination | " | " |
| Breathing | Apnoea | " | " |
| Movement | Difficulty in walking | " | " |
| Center | Non-excited state | " | " |

Consideration: No characteristic symptoms were observed and the toxicity of OSG was considerably low.

(B2) Test for acute toxicity caused by parenteral administration of OSG.
Agents to be tested: OSG.
Test conditions: Room temperature (23° to 25° C.); humidity of from 55% to 60%.
Animals to be tested: Mice, SLC-ddy male and female (Nippon Ika Dobutsu-sha).
Preliminary test: 15 males and 15 females.
Final test: 5 groups, 6 mice per group; 15 males and 15 females.
Average of body weight: Males 23 grams; females 22 grams.
Administration: Intravenous injection.
Calculation: Litchfield and Wilcoxon method.
Test results: For males $LD_5=0.621$ g/kg (the upper limit was 0.676 g/kg and the lower limit was 0.569 g/kg); for females $LD_{50}=0.638$ g/kg (the upper limit was 0.689 g/kg and the lower limit was 0.591 g/kg).
General symptoms: After administration, some mice defecate and urinate.
Posture: Not specified.
Breathing: Apnoea.
Movement: Difficulty in walking.
Center: Non-excited state.
Consideration:
The observation of the symptoms shows that they may take place most frequently at about 50% of lethal dose. The influence of the drug was observed in 5 to 10 seconds after administration, and fore and hind feet were swinged. A number of mice died after 20 seconds. The posture was not constant, but a number of mice were in supination. In one hour after administration, the mice rapidly recovered and moved energetically about.

(C) Clinical results with respect to an essential hypertension patient.
Administration: An 80% ethanol solution (200 ml.) is added to 100 grams of a slightly yellow powder OSG to dissolve the powder therein, and 900 grams of milk sugar (the Japanese pharmacopoeia) is added to the resulting solution. The components are mixed to form granules and dried under reduced pressure to obtain 1 kg of white granules. One gram of this product contains 100 mg of OSG. This product (1.5 grams) is administered to adult humans 2 times, in the morning and evening, before meals. The results obtained are shown in the following Table.

| Nos. | Name | Age | Distinction of sex | Blood pressure before administration | | Blood pressure after administration | | Administration period |
|---|---|---|---|---|---|---|---|---|
| | | | | Systolic (mm Hg) | Diastolic (mm Hg) | Systolic (mm Hg) | Diastolic (mm Hg) | |
| 1 | F. A. | 61 | Male | 220 | 126 | 156 | 89 | One year |
| 2 | K. T. | 85 | Female | 185 | 110 | 158 | 82 | 8 months |
| 3 | S. A. | 66 | Female | 180 | 92 | 135 | 80 | 7 months |
| 4 | S. N. | 53 | Male | 225 | 128 | 138 | 82 | 5 months |
| 5 | K. A. | 81 | Male | 190 | 95 | 165 | 82 | 3 months |

What is claimed is:

1. A process for extraction and purification of a substance referred to as OSG having the following physicochemical properties:
   (1) OSG is a slightly hygroscopic, white or slightly yellow powder;
   (2) OSG exhibits a color reaction of sugar in α-naphthol reaction and orcinol reaction;
   (3) OSG is negative to TCA reaction and ninhydrin reaction;
   (4) OSG is positive in glycyrrhizin reaction;
   (5) when OSG is analyzed by a paper chromatograph method no spots consistent with those of known sugars are observed;
   (6) a hydrolyzate of OSG exhibits a spot consistent with that of glucose or sorbose and exhibits a retention time shorter than that of glucuronic acid; and
   (7) OSG is confirmed to comprise polymeric sugars; having antihypretensive activity from a vegetable oil selected from the group consisting of soybean oil, corn oil, rape seed oil and cotton seed oil, which comprises
   (a) extracting water-soluble components from the vegetable oil, thereby to obtain a first aqueous extract;
   (b) concentrating the aqueous extract;
   (c) adding alcohol to the resulting extract to prepare an alcoholic solution having an alcohol concentration of 85% or higher, thereby precipitating the insoluble matter;
   (d) then removing the precipitate; and
   (e) thereafter removing the alcohol to obtain an aqueous extract product, which contains said substance.

2. The process according to claim 1 wherein said vegetable oil is soybean oil or corn oil.

3. The process according to claim 1 wherein said first aqueous extract is obtained by contacting oil cakes or foots of the vegetable seed with an aqueous solvent.

4. A process for extraction and purification of a substance referred to as OSG having the following physicochemical properties:
  (1) OSG is a slightly hygroscopic, white or slightly yellow powder;
  (2) OSG exhibits a color reaction of sugar in α-naphthol reaction and orcinol reaction;
  (3) OSG is negative to TCA reaction and ninhydrin reaction;
  (4) OSG is positive in glycyrrhizin reaction;
  (5) when OSG is analyzed by a paper chromatograph method no spots consistent with those of known sugars are observed;
  (6) a hydrolyzate of OSG exhibits a spot consistent with that of glucose or sorbose and exhibits a retention time shorter than that of glucuronic acid; and
  (7) OSG is confirmed to comprise polymeric sugars, having antihypretensive activity from a vegetable oil selected from the group consisting of soybean oil, corn oil, rape seed oil and cotton seed oil, which comprises:
  (a) extracting water-soluble components from the vegetable oil thereby to obtain a first aqueous extract;
  (b) concentrating the aqueous extract;
  (c) adding alcohol to the resulting extract to prepare an alcoholic solution having an alcohol concentration of 85% or higher, thereby precipitating the insoluble matter;
  (d) then removing the precipitate;
  (e) thereafter removing the alcohol to obtain an aqueous extract product;
  (f) subjecting said aqueous extract product to an additional purification step if necessary; and
  (g) thereafter concentrating the same to obtain a powdered substance.

5. The process according to claim 4 wherein said vegetable oil is soybean oil or corn oil.

6. The process according to claim 4 wherein said additional optional step (f) for purifying said aqueous extract product is carried out by diluting said aqueous extract product with water and thereafter contacting the diluted product with activated carbon to remove impurities.

7. The process according to claim 4 wherein said additional optional step (f) for purifying said aqueous extract product is carried out by
  (I) diluting the aqueous extract product with water,
  (II) contacting the diluted solution with activated carbon to remove impurities and
  (III) thereafter concentrating the resulting solution to a concentrated solution having a sugar content on a Brix scale of about 50%, thereby depositing a precipitate comprising magnesium lactate as the principal ingredient thereof.

8. The process according to claim 4 wherein said additional optional step for purifying said aqueous extract product is carried out by subjecting said aqueous extract product to a chromatogram to fractionate the same into fractions and thereafter extracting a portion which is positive in α-naphthol reaction.

9. The process of claim 1, wherein the extraction of step (a) is carried out with a solvent selected from water or a 10/90% to 90/10% water-alcohol mixture.

10. The process of claim 9, wherein the water-alcohol mixture of step (a) is 10/40% to 90/60% water-alcohol.

11. The process of claim 9, wherein the amount of solvent in step (a) is about 1 to 5% by weight of the vegetable oil.

12. The process of claim 9, wherein the alcohol in the water-alcohol mixture of step (a) is methanol or ethanol.

13. The process of claim 1, wherein the alcohol added in step (c) results in a final alcohol concentration of about 85% or more.

14. The process of claim 1, further comprising:
  (f) adding water to the thus obtained aqueous extract to obtain a diluted extract;
  (g) admixing active carbon with the water-diluted extract, allowing the admixture to stand and removing said carbon with particles adsorbed thereof;
  (h) removing from the thus treated aqueous extract a solid which precipitates at a sugar content on a Brix scale of about 50% of the extract; and
  (i) drying the aqueous extract to obtain the powder substance having anti-hypertensive activity.

15. The process of claim 1, further comprising:
  (f) separating said solid substance having antihypertensive activity from the liquid.

16. An antihypertensive agent extracted from a vegetable oil selected from the group consisting of soybean oil, corn oil, rape seed oil and cotton oil by water extraction, comprising:
  as an effective component, a substance referred to as OSG having the following physicochemical properties:
  (1) OSG is a slightly hygroscopic, white or slightly yellow powder;
  (2) OSG exhibits a color reaction of sugar in α-naphthol reaction and orcinol reaction;
  (3) OSG is negative to TCA reaction and ninhydrin reaction;
  (4) OSG is positive in glycyrrhizin reaction;
  (5) when OSG is analyzed by a paper chromatograph method no spots consistent with those of known sugars are observed;
  (6) a hydrolyzate of OSG exhibits a spot consistent with that of glucose or sorbose and exhibits a retention time shorter than that of glucuronic acid; and
  (7) OSG is confirmed to comprise polymeric sugars.

17. The anti-hypertensive agent of claim 16, substantially free of magnesium lactate.

18. The antihypertensive agent obtained by the process of claim 1.

* * * * *